(12) United States Patent
Lipman et al.

(10) Patent No.: US 11,273,141 B2
(45) Date of Patent: Mar. 15, 2022

(54) LOW-DOSE CARBACHOL COMPOSITIONS AND METHODS FOR TREATMENT OF NIGHT VISION DISTURBANCE

(71) Applicant: VYLUMA INC., Bridgewater, NJ (US)

(72) Inventors: Jack Martin Lipman, West Milford, NJ (US); Tushar Hingorani, Bridgewater, NJ (US); Kumaresh Soppimath, Skillman, NJ (US)

(73) Assignee: VYLUMA INC., Bridgewater, NJ (US)

(*) Notice: Subject to any disclaimer, the term of this patent is extended or adjusted under 35 U.S.C. 154(b) by 0 days.

(21) Appl. No.: 17/323,781

(22) Filed: May 18, 2021

(65) Prior Publication Data

US 2021/0353584 A1 Nov. 18, 2021

Related U.S. Application Data

(60) Provisional application No. 63/026,654, filed on May 18, 2020.

(51) Int. Cl.
| | | |
|---|---|---|
| *A61K 31/325* | (2006.01) | |
| *A61K 9/00* | (2006.01) | |
| *A61K 47/18* | (2017.01) | |
| *A61K 47/02* | (2006.01) | |
| *A61K 9/08* | (2006.01) | |
| *A61K 47/38* | (2006.01) | |

(52) U.S. Cl.
CPC .......... *A61K 31/325* (2013.01); *A61K 9/0048* (2013.01); *A61K 9/08* (2013.01); *A61K 47/02* (2013.01); *A61K 47/186* (2013.01); *A61K 47/38* (2013.01)

(58) Field of Classification Search
CPC ...... A61K 31/325; A61K 9/0048; A61K 9/08; A61K 47/02; A61K 47/186; A61K 47/38
See application file for complete search history.

(56) References Cited

U.S. PATENT DOCUMENTS

| 8,455,494 B2 | 6/2013 | Kaufinan |
| 2015/0065511 A1 | 3/2015 | Horn et al. |

FOREIGN PATENT DOCUMENTS

| WO | 0064425 A2 | 11/2000 |
| WO | 2010135731 A1 | 11/2010 |
| WO | 2021021646 A1 | 2/2021 |

OTHER PUBLICATIONS

Abdelkader et al., "Clinical outcomes of combined versus separate carbachol and brimonidine drops in correcting presbyopia," Eye and Vision, 2016: 3(31); 6 pgs.
Kato et al., "Effects of brimonidine tartrate 0.1% ophthalmic solution on the pupil, refraction, and light reflex," Scientific Reports, 2018: 8(9003); 5 pgs.
Smolen et al., "Biophasic Availablity of Ophthalmic Carbachol I: Mechanisms of Cationic Polymer- and Surfactant-Promoted Miotic Activity," Journal of Pharmaceutical Sciences, Jun. 1973, 62(6):958-961.
"MIOSTAT—FDA proscribing information, side effects and uses," Alcon, Inc. 2004. Retrieved from the internet: https://www.drugs.com/pro/miostat.html on Feb. 13, 2020; 6 pgs.
"MIOSTAT (Carbachol Intraocular Solution): Uses, Dosage, Side Effects, Interactions, Warning," RXList: Jul. 31, 2017. Retrieved from the internet: https://www.rxlist.com/miostat-drug.htm#description on Feb. 13, 2020; 5 pgs.
Li, Md et al., "Low-Concentration Atropine Eye Drops for Myopia Progression," Asia Pac J Ophthalmol (Phila), 2019; 8(5):360-365.
Ogle et al., "Quantitative study of pupil response to miotic drugs," Investigative Ophtalmology, Apr. 1966; 5(2):176-185.
Randazzo et al., "Pharmacological management of night vision disturbances after refractive surgery: Results of a randomized clinical trial," J Cataract Refract Surg., Sep. 2005; 31(9):1764-1772. Abstract Only.
Wu et al., "The long-term results of using low-concentration atropine eye drops for controlling myopia progression in schoolchildren," J Ocul Pharmacol Ther., Oct. 2011; 27(5):461-466. Abstract only.

*Primary Examiner* — Sarah Pihonak
(74) *Attorney, Agent, or Firm* — Umberg Zipser LLP

(57) ABSTRACT

Ophthalmic formulations for acute and transient treatment of night vision disturbance syndrome (NVD) are presented. Preferred formulations comprise carbachol at very low concentrations that were demonstrated to unexpectedly provide an acute and transient therapeutic effect for a desirable magnitude and period of time.

10 Claims, 10 Drawing Sheets

LOW-DOSE CARBACHOL COMPOSITIONS AND METHODS FOR TREATMENT OF NIGHT VISION DISTURBANCE

This application claims priority to our U.S. Provisional Patent Application with the Ser. No. 63/026,654, which was filed May 18, 2020, and which is incorporated by reference herein.

FIELD OF THE INVENTION

The field of the invention is ophthalmic compositions comprising carbachol and methods therefore, especially as it relates to low-dose carbachol compositions for treatment of night vision disturbance syndrome.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Night vision disturbances (NVD), especially after refractive surgery are unfortunately relatively common and adversely affect many ordinary tasks under low-light conditions. Most often, individuals suffering from NVD experience glare, starbursts, double vision, and halo around brighter objects under low-light conditions or darkness. Given the limited time during which an individual experiences NVD, therapeutic interventions should be restricted to those that are acute and transient to provide prompt effect upon administration of a drug, but also of sufficiently short duration so as to not interfere with vision under non-scotopic conditions.

A study performed using aceclidine (1-azabicyclo[2.2.2] octan-3-yl acetate), typically used to treat open-angle glaucoma, provided reduction in some symptoms (see *J Cataract Refract Surg.* 2005 September; 31(9): 1764-72) in selected patient after refractive surgery. However, the physiological effect of aceclidine was relatively extended. Moreover, aceclidine is known to have significant side effects, including increased salivation and bradycardia, which significantly limits desirability and compliance once prescribed. In another known example, WO 00/64425 describes the use of miotic agents, such as cholinomimetic active agents and cholinesterase inhibitors, in combination with one or more hypertonic agents, such as sulfacetamide and derivatives thereof to treat visual disorders characterized by reduced contrast sensitivity. Unfortunately, the duration of the drug effect was once more relatively long (up to 14 hours), and thus renders the formulations unsuitable for acute and transient use.

In still further examples, U.S. Pat. No. 8,455,494 and WO 2010/135731 describe the use of drug combinations of one or more parasympathomimetic drugs or cholinesterase inhibitors with one or more alpha agonists or antagonists to temporarily treat presbyopia. However, while such formulations were to at least some degree effective in the treatment of presbyopia, use in the treatment of NVD was not contemplated. Similarly, WO 2020/072971 teaches stable aqueous topical ophthalmic composition comprising about 0.1% to 10% of cevimeline and other agents for treatment of dry eye disease but does not contemplate use of such formulations for acute and transient treatment of NVD.

Carbachol (carbamoylcholine) is a parasympathomimetic agent that stimulates both muscarinic and nicotinic receptors. In topical ocular and intraocular administration its principal effects are miosis and increased aqueous humor outflow, and a change in refraction to at least some degree (see e.g., *Investigative Ophthalmology & Visual Science* April 1966, Vol. 5, 186-195). Carbachol is primarily used in the treatment of glaucoma and is used during ophthalmic surgery. For example, CARBASTAT (Carbachol Intraocular Solution, USP, Novartis) or MIOSTAT (Carbachol Intraocular Solution, USP, Novartis) are administered at a concentration of 0.1 mg/mL via intraocular injection to produce miosis during surgery and to reduce the intensity of intraocular pressure elevation in the first 24 hours after cataract surgery. Similarly, ISOPTO CARBACHOL (Carbachol Ophthalmic Solution, Alcon; discontinued) was intended for topical administration at a concentration of 1.5% or 3% to treat glaucoma. However, this drug formulation has not been found by the FDA to be safe and effective, and this labeling has therefore not been approved by FDA.

Thus, even though various compositions and methods of treating NVD and other ophthalmic conditions are known in the art, all or almost all of them suffer from several drawbacks, particularly where acute and transient treatment is required. Therefore, there remains a need for improved compositions and methods for acute and transient treatment of ophthalmic conditions, and especially NVD.

SUMMARY OF THE INVENTION

The inventive subject matter is directed to various compositions and methods of use of carbachol at low concentrations to provide acute and transient treatment of NVD. Most typically, such compositions are topically applied and comprise carbachol in quantities of equal or less than about 0.75% (e.g., about 0.5% or about 0.3%) and achieve a prompt miotic effect sufficient to reduce NVD symptoms with a duration of about 3-4 hours. Notably, the so obtained miotic effect will not be sufficient to treat presbyopia.

In one aspect of the inventive subject matter, the inventors contemplate a method of acute and transient treatment of night vision disturbance in an individual. Most typically, such methods will include a step of topically administering a carbachol composition to one or both eyes of an individual, and the carbachol is present in the composition in an amount of equal or less than about 0.75% (e.g., equal or less than about 0.50% or between about 0.3% and 0.50%). It is further generally preferred that in such methods carbachol is the sole miotic agent.

Where desired, it is contemplated that the carbachol composition may also include benzalkonium chloride in an amount that increases delivery of carbachol to the pupillary muscle. For example, benzalkonium chloride may be present in an amount of at least 0.02%. In some embodiments of contemplated methods, the miotic effect is equal or less than 30%, equal or less than 20% reduction in pupillary diameter, or equal or less than 15% reduction in pupillary diameter, or equal or less than 10% reduction in pupillary diameter. Most typically, the treatment will reduce glare, starburst, halo, and/or double vision under low-light conditions or in darkness. While contemplated methods are suitable for all individuals (e.g., healthy individuals, individuals post refractive surgery), it is contemplated that in some embodiments the individual has not undergone refractive surgery.

In further contemplated embodiments, the acute and transient treatment has a duration of equal or less than 3 hours at a reduction of pupillary diameter of about 2 mm, or has a duration of equal or less than 2 hours at a reduction of pupillary diameter of about 2 mm, or has a duration of equal or less than 1 hours at a reduction of pupillary diameter of about 2 mm. Preferably, but not necessarily, the acute and transient treatment is an on-demand and non-curative treatment.

Therefore, in another aspect of the inventive subject matter, the inventors also contemplate a topical ophthalmic composition for acute and transient treatment of night vision disturbance that comprises carbachol in an amount of equal or less than about 0.75%. Most typically, carbachol is the sole miotic agent in such compositions.

For example, the topical ophthalmic composition may comprise carbachol in an amount of equal or less than about 0.50%, or in an amount of between about 0.3% and 0.50%. Preferably, but not necessarily, benzalkonium chloride may be included in an amount of at least 0.0001%, or in an amount of at least 0.02%. Thus, it is noted that benzalkonium chloride may be present in an amount that increases delivery of carbachol to the pupillary muscle.

Preferably, but not necessarily, the topical ophthalmic composition will have a pH of between 6.0 and 7.0, and/or may comprise a buffer. Where a buffer is present, it is contemplated that the buffer will preferably have a concentration of between 10 mM and 100 mM. It is further generally preferred that the topical ophthalmic composition will have a viscosity of between 10 cP and 250 cP (e.g., between 150 cP and 200 cP).

Therefore, and viewed from a different perspective, the inventors contemplate the use of carbachol as sole active agent in acute and transient treatment of night vision disturbance. For example, such acute and transient treatment may a duration of equal or less than 4 hours or equal or less than 3 hours. For example, in some embodiments the acute and transient treatment has a duration of equal or less than 3 hours at a reduction of pupillary diameter of about 2 mm. Most typically, contemplated compositions comprise carbachol in an amount of equal or less than about 0.75% or equal or less than about 0.50%. Such compositions will reduce at least one of glare, starburst, halo, and double vision, typically in an on-demand and non-curative manner.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
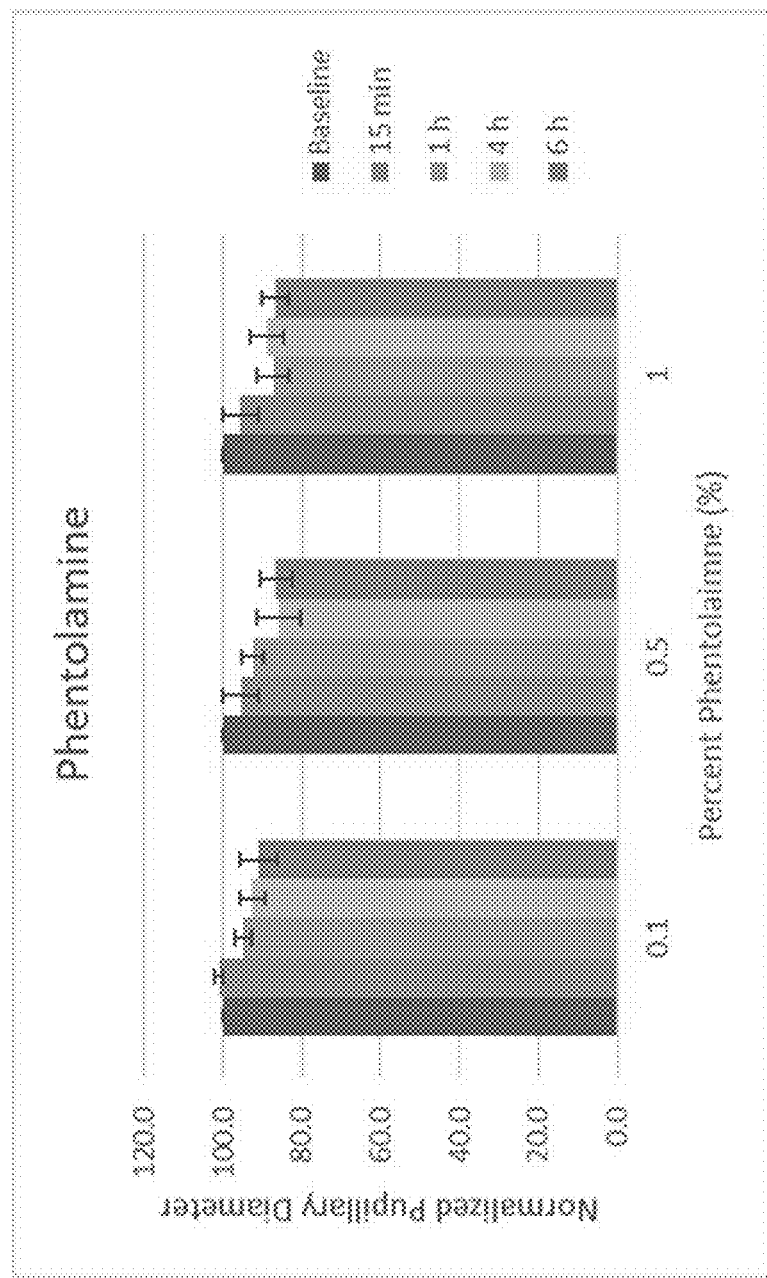
FIG. 1 is a graph depicting strength and duration of miotic effect of phentolamine in a rabbit eye model.

It has been generally established that treatment of NVD requires a significantly high concentration of a miotic agent to achieve a therapeutically effective miotic effect. However, the time for the pupil to recover to half of maximal constriction ($t_{1/2r}$) for various miotic drugs is commonly estimated to be 7-8 hours (see e.g., *Investigative Ophthalmology & Visual Science* April 1966, Vol. 5, 186-195). Viewed from a different perspective, it is commonly understood by the skilled artisan that the strength and the duration of the miotic effect tend to be correlated. Unfortunately, in practice, treatment of NVD only requires correction during low light conditions such as an evening or night commute that should not subsequently affect vision after the low light conditions have ceased. Consequently, long-term miosis (e.g., 7-15 hours) is undesirable for treatment of NVD. Therefore, compositions and methods are desired that provide an acute and transient miotic effect that is on one hand sufficiently strong to treat NVD but on the other hand sufficiently limited in time.

The inventors have now discovered various compositions and methods using carbachol that allow for acute and transient treatment of NVD. In especially preferred aspects, the compositions are topically applied ophthalmic formulations that include carbachol as the principal active agent at a very low concentration of, for example, about equal or less than 0.75%, or about equal or less than 0.50%, or about 0.3% to 0.5%. Unexpectedly, the inventors discovered that such low concentrations afforded a significant therapeutic effect with regard to NVD, typically achieving pupillary constriction of 1-2 mm, while having a controlled limited therapeutic duration, typically between 2-4 hours.

As used herein, the term "treat" or "treatment" when used in conjunction with NVD is not intended to mean curative treatment, but refers to alleviation, reduction, or even complete elimination of one or more symptoms of NVD. In this context, it should also be appreciated that the compositions and methods of treatment contemplated herein will effect a temporary reduction of the pupillary diameter of about 10-30%, which would be unsuitable or even entirely ineffective in a treatment of presbyopia. Interestingly, however, such limited reduction in pupillary size (particularly under low light conditions) will typically cover most of the area treated in surgical corneal correction such as LASIK procedures. Therefore, administration of contemplated compounds and formulations is non-curative with respect to the condition that produces NVD.

The term "acute and transient" when used in conjunction with treatment is meant to refer to a treatment that produces upon administration of a therapeutic agent (here: carbachol formulations as presented herein administered as eye drops) a treatment effect within no more than 60 minutes that lasts no more than 4 hours. Thus, most forms of acute and transient treatments can be implemented as on-demand and temporary measure to reduce one or more symptoms of NVD. The term "NVD" or "night vision disturbance" as used herein refers to perception of glare, starburst, halo, and/or double vision that are noted only under low-light conditions (such as dusk) or darkness (night). Viewed from a different perspective, NVD is typically associated with scotopic vision that is predominantly based on rod cells (non-color vision in human), typically occurring at luminance levels at or below $10^{-3}$ cd/m$^2$.

It should further be appreciated that contemplated and preferred compositions and methods are intended to treat NVD, which are generally associated with visual disturbances at longer distances (i.e., focal distances well beyond reading distances typically seen in treatment of presbyopia). Such disturbances will typically be at distances of at least 1 m, or at least 5 m, or at least 10 m, or at least 25 m, or at least 50 m, and significantly longer distances. Moreover, contemplated and preferred compositions and methods are intended to treat conditions in low-light environments such as evening and night. Thus, it should be noted that contemplated compositions and methods treat NVD without (substantially) affecting the perception of overall brightness. In addition, it should be appreciated that NVD as contemplated herein need not only be due to refractive surgery, but may have various other etiologies, including ageing, cataracts, excessive sunlight exposure, retinitis pigmentosa, vitamin A and/or zinc deficiency, etc.

In one exemplary embodiment, a formulation for topical administration of carbachol for the treatment of NVD comprises carbachol at a concentration of 0.50%. Most typically, the formulation will be buffered with a borate buffer to a pH of 6.5 or 7.0, and the buffer will have a buffer strength of 50 mM. The formulation will further comprise benzalkonium chloride as a preservative and is typically present at a concentration of 0.02%, which has shown to increase the delivery of carbachol to the pupillary muscle. Most preferably, the formulation has a viscosity of between 150 cP and 250 cP, and the formulation will be packaged in a multi-use eye dropper container to enable multiple administrations in a sterile manner. The table below exemplarily shows selected formulation compositions suitable for use in conjunction with the teachings presented herein.

| Ingredient | Grade | Function | Quantity % (mg/mL) |
| --- | --- | --- | --- |
| Carbachol | USP | API | 0.02-3.0% (0.2-30 mg/mL) |
| Sodium Chloride | USP | Tonicity agent | 0.05-0.9% (0.5-9.0 mg/mL) |
| Hypromellose 2910 | USP | Viscosity modifier | 0.2-1.0% (2-10 mg/mL) |
| Boric Acid | USP | Buffering agent | (0.02-0.62%) 0.2-6.2 mg/mL |
| Sodium Hydroxide | USP | pH adjuster | q.s. to pH 5.5-7.5 |
| Benzalkonium Chloride | USP | Preservative | 0.05-0.02% (0.5-0.2 mg/mL) |
| Water for Injection | NF | Vehicle | q.s. to 100% (1.0 mL) |

As will be readily appreciated, contemplated formulations will be available in a range of concentrations commonly required by medical practitioners for treatment of NVD, and particularly for acute and transient treatment of NVD. Consequently, carbachol will typically be present in formulations in an amount of equal or less than about 0.75 wt %, or in an amount of equal or less than about 0.70 wt %, or in an amount of equal or less than about 0.60 wt %, or in an amount of equal or less than about 0.50 wt %, or in an amount of equal or less than about 0.40 wt %, or in an amount of equal or less than about 0.30 wt %, and in some cases in an amount of equal or less than 0.20 wt %. For example, the carbachol may be present in the ophthalmic composition in an amount of between about 0.01% and about 0.05 wt %, or in an amount of between about 0.05% and about 0.10 wt %, or in an amount of between about 0.10% and about 0.05 wt %, or in an amount of between about 0.05% and about 0.10 wt %, or in an amount of between about 0.10% and about 0.20 wt %, or in an amount of between about 0.20% and about 0.30 wt %, or in an amount of between about 0.30% and about 0.40 wt %, or in an amount of between about 0.30% and about 0.50 wt %, or in an amount of between about 0.40% and about 0.60 wt %, or in an amount of between about 0.50% and about 0.70 wt %, or in an amount of between about 0.60% and about 0.80 wt %, and even higher. For example, suitable carbachol concentrations will be about 0.2%, or about 0.3%, or about 0.4%, or about 0.5%, or about 0.6%, or about 0.7% or about 0.75%.

As will be readily appreciated, carbachol for the preparation of contemplated formulations may be carbachol or any suitable pharmaceutically acceptable salt thereof, including mineral salts (e.g., HCl salt) and organic salts (e.g., sulfate). Similarly, where desired, the carbachol may also be used in any suitable prodrug form.

For example, in one exemplary embodiment, the concentration of carbachol in contemplated carbachol formulations is from about 0.015% to about 0.025% (w/w); or from about 0.025% to about 0.035% (w/w), or from about 0.035% to about 0.045% (w/w), or from about 0.045% to about 0.055% (w/w), or from about 0.055% to about 0.065% (w/w), or from about 0.065% to about 0.75% (w/w), or from about 0.075% to about 0.085% (w/w) or from about 0.085% to about 0.1% (w/w).

In another exemplary embodiment, the concentration of carbachol in contemplated carbachol formulations is from about 0.025% to about 0.050% (w/w); or from about 0.050% to about 0.075% (w/w), or from about 0.075% to about 0.1% (w/w), or from about 0.1% to about 0.15% (w/w), or from about 0.15% to about 0.25% (w/w), or from about 0.25% to about 0.50% (w/w), or from about 0.50% to about 0.75% (w/w) or from about 0.75% to about 1.00% (w/w).

It is further contemplated that the compositions presented herein will comprise a buffer, and suitable buffers are generally buffers that stabilize the pH of the contemplated liquid formulations in a near-neutral pH range, for example between pH 4.0 and 9.0, or between pH 4.5 and 8.0, and more preferably between pH 6.0 and 7.5. Therefore, and most typically the pH of contemplated formulations will be equal or less than 8.0 and more typically equal or less than 7.5, and most typically equal or less than 7.0, but higher than 4.5, more typically higher than 5.0, and most typically higher than 5.2. Thus, contemplated pH ranges for the carbachol formulations appropriate for use herein include pH 5.0-7.0, pH 5.5-7.5, pH 6.0-7.0, pH 6.0-7.5, pH 6.5-7.5, and pH 6.5-7.0. For example, suitable carbachol compositions may have a pH of 5.0 (+/−0.2), or a pH of 5.5 (+/−0.2), or a pH of 6.0 (+/−0.2), or a pH of 6.5 (+/−0.2), or a pH of 7.0 (+/−0.2), or a pH of 7.5 (+/−0.2).

Most typically, a buffer or buffer system will be included to stabilize the pH of the formulation, and all pharmaceutically acceptable buffers are contemplated for use herein, including organic and inorganic buffers as well as amphoteric buffers. Preferably, but not necessarily, the buffer system and/or buffer may have a buffer strength that is relatively low, for example, equal or less than 100 mM, equal or less than 75 mM, equal or less than 60 mM, equal or less than 50 mM, or between 5 mM and 50 mM (e.g., about 10 mM, about 20 mM, about 30 mM, about 40 mM). Therefore, in exemplary embodiments, the buffering system is in the pharmaceutical composition in a concentration of from about 10 mM to about 75 mM, or from about 10 mM to about 60 mM, or from about 0.1 mM to about 60 mM, or from about 0.1 mM to about 55 mM, or from about 0.1 mM to about 50 mM, or from about 5 mM to about 60 mM, or from about 0.1 mM to about 10 mM, or from about 1 mM to about 10 mM, or from about 9 mM to about 20 mM, or from about 15 mM to about 25 mM, or from about 19 mM to about 29 mM, or from about 24 mM to about 34 mM, or from about 29 mM to about 39 mM, or from about 34 mM to about 44 mM, or from about 39 mM to about 49 mM, or from about 44 mM to about 54 mM, or from about 19 mM to about 54 mM, or from about 25 mM to about 54 mM.

As noted before, it should be appreciated that there are many types of buffer systems and buffers known in the art, and all of those are deemed suitable for use herein, including buffer systems comprising an acid and a salt of the acid, a first and a second salt (e.g., monobasic and dibasic salt), and amphoteric buffer molecules. For example, suitable buffer systems with an acid and a salt of the acid include citric acid/sodium citrate buffers, ethanoic acid/sodium ethanoate buffers, boric acid/sodium borate, while suitable buffers having a first and a second salt include monobasic sodium phosphate/dibasic sodium phosphate, or monobasic sodium phosphate/sodium citrate, etc. Similarly, suitable amphoteric buffer molecules include HEPES, MOPS, PIPES, MES, etc.

Where desired, the formulation may also include one or more chelating agents, and particularly metal ion chelators. For example, suitable chelators include various bicarboxylic acids, tricarboxylic acids, and aminopolycarboxylic acids such as ethylenediaminetetraacetic acid (EDTA), ethylene glycol-bis(β-aminoethyl ether)-N,N,N',N'-tetraacetic acid (EGTA), and penta(carboxymethyl)diethylenetriamine (DTPA), and salts and hydrates thereof. For example, exemplary chelator concentrations are between 10 μg/ml and 50 μg/ml, between 50 μg/ml and 250 μg/ml, and between 100 μg/ml and 500 μg/ml. Viewed form a different perspective, chelator concentrations of equal or less than 0.03 wt %, or equal or less than 0.02 wt %, or equal or less than 0.01 wt % are especially advantageous.

Suitable chelating agents include monomeric polyacids such as EDTA, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccmic acid (DMSA), aminotrimethylene phosphonic acid (ATPA), citric acid, ophthalmologically acceptable salts thereof, and combinations of any of the foregoing. Further suitable chelating agents include pyrophosphates, tripolyphosphates, and, hexametaphosphates, chelating antibiotics such as chloroquine and tetracycline, nitrogen-containing chelating agent containing two or more chelating nitrogen atoms within an imino group or in an aromatic ring (e.g., diimines, 2,2'-bipyridines, etc.), and various polyamines such as cyclam (1,4,7,11-tetraazacyclotetradecane), N—(C1-C30 alkyl)-substituted cyclams (e.g., hexadecyclam, tetramethylhexadecylcyclam), diethylenetriamine (DETA), spermine, diethylnorspermine (DENSPM), diethylhomo-spermine (DEHOP), and deferoxamine (N'-[5-[[4-[[5-(acetylhydroxyamino)pentyl]amino]-1,4-dioxobutyl]hydroxy-amino]pentyl]-N'-(5-aminopentyl)-N-hydroxybutanediamide; also known as desferrioxamine B and DFO).

In still further contemplated aspects, the formulations may also include a salt as a tonicity agent. With respect to suitable salts it is contemplated that the salt is a pharmaceutically acceptable salt, and especially NaCl, at a concentration of at least 0.2 wt %, or at least 0.4 wt %, or at least 0.5 wt %, or at least 0.7 wt %. For example, suitable salt concentrations are between 0.2 wt % and 1.1 wt %, 0.4 wt % and 0.9 wt %, or 0.3 wt % and 0.7 wt %. Depending on the particular salt concentration, additional tonicity agents may be added, and suitable tonicity agents include glycerol, thioglycerol, mannitol, lactose, propylene glycol, and dextrose. The amount of tonicity adjusting agent used can be adjusted to obtain osmolality of the formulations in the range of 260 to 340 mOsm/kg. An osmometer can be used to check and adjust the amount of tonicity adjusting agent to be added to obtain the desired osmolality.

As contemplated formulations are used as an ophthalmic formulation, it is generally preferred that the formulation also includes a viscosity modifier to adjust the viscosity of the formulation to a dynamic viscosity of between 10 and 250 cP (centipoise), and more preferably above 50 cP, or above 75 cP, or above 100 cP, or above 125 cP, or above 150 cP, or above 175 cP, or above 200 cP, or above 225 cP, or even above 250 cP. However, it is generally preferred that the viscosity is less than 300 cP. Therefore, suitable viscosity ranges are between 20 and 50 cP, and more typically between 50-100 cP, or between 50-150 cP, or between 75-150 cP, or between 75-200 cP, or between 100-250 cP, or between 100-200 cP, or between 150-250 cP, or between 150-200 cP. Such viscosity ranges are somewhat higher than most ophthalmic formulations and are thought to assist in achieving an acute treatment effect.

While there are numerous viscosity modifiers known in the art such as various polymers, glycerol, and polysaccharidic polymers (all of which are contemplated herein), especially preferred viscosity modifiers include cellulosic viscosity modifiers. For example, particularly preferred cellulosic viscosity modifiers include modified and unmodified hydroxyethyl cellulose, hydroxypropyl cellulose, and hydroxypropyl methylcellulose. As will be readily appreciated, the exact quantity of the viscosity modifier may vary depending on the type of modifier used and desired final viscosity. The person of ordinary skill will be readily able to adjust the viscosity to a desired measure using viscometers (e.g., rotational, vibration, etc.) well known in the art.

In exemplary embodiments, suitable concentrations of the viscosity modifier in contemplated ophthalmic formulations may be any value less than 5% (w/w). For example, suitable concentrations of the viscosity modifier include 0.01% to 4.99% (w/w); or 0.05% to 4.50% (w/w), 0.10% to 3.50% (w/w), 0.15% to 3.00% (w/w), 0.20% to 2.50% (w/w), 0.21% to 2.20% (w/w), 0.22% to 2.10% (w/w), 0.23% to 2.00% (w/w), 0.24% to 1.90% (w/w); 0.25% to 1.80% (w/w), 0.26% to 1.70% (w/w), 0.27% to 1.60% (w/w), 0.28% to 1.50% (w/w), 0.29% to 1.40% (w/w), 0.30% to 1.30% (w/w), 0.31% to 1.2% (w/w), 0.32% to 1.10% (w/w), 0.33% to 1.00% (w/w), 0.34% to 0.90% (w/w); 0.35% to 0.80% (w/w), 0.36% to 0.75% (w/w), 0.37% to 0.70% (w/w), 0.38% to 0.69% (w/w), 0.39% to 0.68% (w/w), 0.40% to 0.67% (w/w), 0.41% to 0.66% (w/w), 0.42% to 0.65% (w/w), 0.43% to 0.64% (w/w), 0.44% to 0.63% (w/w), 0.45% to 0.62% (w/w), 0.45% to 0.61% (w/w), 0.45% to 0.60% (w/w), 0.45% to 0.59% (w/w), 0.45% to 0.58% (w/w), 0.45% to 0.57% (w/w), 0.45% to 0.56% (w/w), 0.45% to 0.55% (w/w), 0.46% to 0.54% (w/w), 0.47% to 0.53% (w/w), 0.48% to 0.52% (w/w) or 0.49% to 0.51% (w/w).

Therefore, appropriate concentrations of the viscosity modifier in contemplated ophthalmic formulations include 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, 0.30%, 0.31%, 0.32%, 0.33%, 0.34%, 0.35%, 0.36%, 0.37%, 0.38%, 0.39%, 0.40%, 0.41%, 0.42%, 0.43%, 0.44%, 0.45%, 0.46%, 0.47%, 0.48%, 0.49%, 0.50%, 0.51%, 0.52%, 0.53%, 0.54%, 0.55%, 0.56%, 0.57%, 0.58%, 0.59%, 0.60%, 0.61%, 0.62%, 0.63%, 0.64%, 0.65%, 0.66%, 0.67%, 0.68%, 0.69%, 0.70%, 0.71%, 0.72%, 0.73%, 0.74%, 0.75%, 0.76%, 0.77%, 0.78%, 0.79%, 0.80%, 0.81%, 0.82%, 0.83%, 0.84%, 0.85%, 0.86%, 0.87%, 0.88%, 0.89%, 0.90%, 0.91%, 0.92%, 0.93%, 0.94%, 0.95%, 0.96%, 0.97%, 0.98%, 0.99%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 3.10%, 3.20%, 3.30%, 3.40%, 3.50%, 3.60%, 3.70%, 3.80%, 3.90%, 4.00%, 4.10%, 4.20%, 4.30%, 4.40%, 4.50%, 4.60%, 4.70%, 4.80%, 4.90% and 4.99% (w/w).

As needed or desired, contemplated formulations will further include one or more preservatives such as benzalkonium chloride, cetrimide or cetrimonium chloride or bromide, benzododecinium bromide, miramine, cetylpyridinium chloride, polidronium chloride or polyquaternium-1, polyquatemium-42 (also known as polixetonium), sepazonium chloride; mercurial derivatives such as the phenylmercury salts (acetate, borate or nitrate), mercuriothiolate sodium (otherwise called thiomersal or thimerosal) and mercurobutol; amidines such as chlorhexidine digluconate or polyhexamethylene biguanide (PHMB); alcohols such as chlorobutanol or phenylethanol or benzyl alcohol or phenol or m-cresol or phenoxyethanol; parabens or esters such as parahydroxybenzoic acid, methylparaben, and propylparaben).

With respect to the sterilization of contemplated formulations it should be appreciated that contemplated formulations may be sterilized using all known manners of sterilization, including filtration through 0.22 micron filters, heat sterilization, autoclaving, radiation (e.g., gamma, electron beam, microwave). However, it is generally preferred that the compositions presented herein are sterilized by autoclaving the polymer phase and the drug product phase is filter sterilized. Thus, it should be appreciated that in some embodiments the production of contemplated compositions will include a first production train in which a first aqueous solution is prepared that contains carbachol and all other ingredients except the viscosity modifier, and a second production train in which a second aqueous solution is prepared that contains the viscosity modifier. The carbachol containing solution is then sterilized using autoclaving, while the solution containing the viscosity modifier is sterilized using filter sterilization. Both sterilized solutions are then combined into a sterile final solution that can then be packaged into a single-use or multi-use container. An exemplary process suitable for use herein is described in U.S. Pat. No. 10,610,525, incorporated by reference herein.

In view of the above, it should therefore be appreciated that the compositions according to the inventive subject matter are formulated such that a miotic (i.e., treatment) effect will be achieved within a relatively short time (i.e., acute treatment) and will have a relatively short duration (i.e., transient treatment) while providing a therapeutic effect with respect to NVD (i.e., reduce or eliminate at least one of glare, halo, double vision, and starburst).

Most typically, acute treatment will result in a maximum pupillary constriction within no more than 90 min, or no more than 80 min, or no more than 70 min, or no more than 60 min, or no more than 50 min, or no more than 40 min, or no more than 30 min, or no more than 20 min, or no more than 15 min, or no more than 10 min from administration of the ophthalmic composition. Thus, maximum pupillary constriction may be observed within 5-10 minutes, or within 10-20 minutes, or within 20-30 minutes, or within 30-40 minutes, or within 40-50 minutes, or within 50-60 minutes, or within 60-70 minutes, or within 70-90 minutes. However, maximum pupillary constriction will most typically be achieved within about 50 min, about 60 min, or about 70 min.

With respect to transient treatment, it is contemplated that the duration of the miotic effect between administration and recovery to 70% of initial pupillary diameter is at least 10 min, or at least 20 min, or at least 30 min, or at least 40 min, or at least 60 min, or at least 90 min, or at least 120 min, or at least 180 min, or at least 240 min, or at least 300 min, or at least 360 min, and even more in some cases (duration can be determined using laser pupillometry in a rabbit eye test model). However, it is generally preferred that the duration of the miotic effect between administration and recovery to 70% of initial pupillary diameter is no longer than 6 hours, or no longer than 5 hours, or no longer than 4.5 hours, or no longer than hours, or no longer than 3.5 hours, or no longer than 3 hours, or no longer than 2.5 hours, or no longer than 2 hours. Thus, in at least some embodiments the duration of the miotic effect between administration and recovery to 70% of initial pupillary diameter may be between about 60-90 minutes, or between about 90 and 120 minutes, or between about 120-180 minutes, or between 3-4 hours, or between 4-5 hours, and in some cases even between 5-6 hours. For example, suitable formulations will result in a duration of the miotic effect between administration and recovery to 70% of initial pupillary diameter of 1-3 hours, 2-4 hours, or 3-5 hours.

Most typically, the miotic effect produced by contemplated compositions will produce a reduction in pupillary diameter (as measured from before administration under normoptic conditions) of at least 5%, or at least 7%, or at least 10%, or at least 12%, or at least 14%, or at least 16%, or at least 18%, or at least 20%, or at least 22%, or at least 25%, or at least 30%, or at least 35%, or at least 40%, or at least 50%, but most typically no more than 30%, or no more than 25%, or no more than 22%, or no more than 20%, or no more than 18%, or no more than 15%. Therefore, contemplated reductions in pupillary diameter (as measured from before administration under normoptic conditions) will be between 2-5%, or between 5-7%, or between 7-10%, or between 10-12%, or between 12-15%, or between 15-17%, or between 17-20%, or in some cases even between 20-25%, or between 25-35%, or between 35-45%, or between 45-50%, or even higher. When measured in mm, the reduction in pupillary diameter (as measured from before administration under normoptic conditions) will preferably be at least 0.5 mm, or at least 0.7 mm, or at least 0.9 mm, or at least 1.1 mm, or at least 1.3 mm, or at least 1.5 mm, or at least 1.7 mm, or at least 1.9 mm, or at least 2.1 mm, or at least 2.3 mm, or at least 2.5 mm. Most preferably, the reduction in pupillary diameter will be between 0.7-1.3 mm, or between 1.0-1.5 mm, or between 1.3-1.7 mm, or between 1.5-2.0 mm, or between 1.0-2.0 mm, or between 1.5-2.5 mm. Therefore, preferred reduction in pupillary diameter (as measured from before administration under normoptic conditions) will be 1.8 mm (+/−0.1 mm), 1.8 mm (+/−0.2 mm), 1.9 mm (+/−0.1 mm), 1.9 mm (+/−0.2 mm), 2.0 mm (+/−0.1 mm), 2.0 mm (+/−0.2 mm), 2.1 mm (+/−0.1 mm), 2.1 mm (+/−0.2 mm), 2.2 mm (+/−0.1 mm), or 2.2 mm (+/−0.2 mm), For example, an acute and transient treatment may have a duration of equal or less than 3 hours at a reduction of pupillary diameter of about 2 mm, or a duration of equal or less than 2.5 hours at a reduction of pupillary diameter of about 2 mm, or a duration of equal or less than 2 hours at a reduction of pupillary diameter of about 2 mm, or a duration of equal or less than 1.5 hours at a reduction of pupillary diameter of about 2 mm. In other examples, the acute and transient treatment may have a duration of equal or less than 3 hours at a reduction of pupillary diameter of about 1.8 mm, or a duration of equal or less than 2.5 hours at a reduction of pupillary diameter of about 1.8 mm, or a duration of equal or less than 2 hours at a reduction of pupillary diameter of about 1.8 mm, or a duration of equal or less than 1.5 hours at a reduction of pupillary diameter of about 1.8 mm. In still further examples, the acute and transient treatment may have a duration of equal or less than 3 hours at a reduction of pupillary diameter of about 1.5 mm, or a duration of equal or less than 2.5 hours at a reduction of pupillary diameter of about 1.5 mm, or a duration of equal or less than 2 hours at a reduction of pupillary diameter of about 1.5 mm, or a duration of equal or less than 1.5 hours at a reduction of pupillary diameter of about 1.5 mm.

Notably, and as shown in more detail further below, the inventors also discovered that benzalkonium chloride may enhance the miotic effect. While not wishing to be bound by any theory or hypothesis, benzalkonium chloride is thought to assist carbachol to penetrate to the pupillary muscle, and as such the effective concentration of benzalkonium chloride will be higher. Most typically, concentrations of benzalkonium chloride will be higher than those normally used for antimicrobial activity.

For example, where benzalkonium chloride (BAC; N-Alkyl-N-benzyl-N,N-dimethyl-ammonium chloride) or other quaternary ammonium-based surfactant is being used to enhance carbachol penetration to the pupillary muscle, it should be noted that the concentration of the BAC will typically be above the concentration ordinarily used for antimicrobial effect. Most preferably, the concentration of BAC or other quaternary ammonium-based surfactant in contemplated formulations will be at least 0.010%, or at least 0.012%, or at least 0.014%, or at least 0.016%, or at least 0.018%, or at least 0.020%, or at least 0.022%, or at least 0.024%, or at least 0.026%, or at least 0.028%, or at least 0.030%, or at least 0.033%, or at least 0.036%, or at least 0.039%, or at least 0.042%, or at least 0.045%, or at least 0.050%, or even higher. Therefore, suitable BAC or other quaternary ammonium-based surfactant concentrations may be in the range of between 0.010-0.014%, or between 0.012-0.016%, or between 0.014-0.018%, or between 0.016-0.020%, or between 0.018-0.022%, or between 0.020-0.024%, or between 0.022-0.026%, or between 0.024-0.028%, or between 0.026-0.030%, or between 0.028-0.032%, or between 0.030-0.035%, or between 0.015-0.025%, or between 0.010-0.030%, or between 0.015-0.035%. Thus, and viewed form a different perspective, the concentration of BAC or other quaternary ammonium-based surfactant in contemplated formulations will be at least 0.015%, or at least 0.017%, or at least 0.0192%, or at least 0.017%, or at least 0.021%, or at least 0.023%, or at least 0.025%, or at least 0.030%, or even higher. In still further contemplated aspects, the concentration of the BAC or other quaternary ammonium-based surfactant may also be significantly lower, such as for example, about 0.001%, or about 0.002%, or about 0.003%, or about 0.004%, or about 0.005%, or higher.

EXAMPLES

Conceptually, there are multiple classes of drugs available that induce miosis, including alpha-1 agonists (e.g., dapiprazole, doxazosin) as well as alpha-2 agonists (e.g., brimonidine) that both act on the iris dilator and that both inhibit pupil dilation. On the other hand, cholinergic agonists that act on iris sphincter and increase pupil constrictions (e.g., carbachol, pilocarpine, aceclidine) can be used, as well as cholinesterase inhibitors that act on the iris sphincter and increase pupil constrictions (e.g., rivastigmine, galantamine, tacrine, neostigmine). However, as established below, not all classes and even compounds of the same class acted equally well. Indeed, the inventors surprisingly discovered that carbachol had a significant miotic effect at concentrations that enabled a desirably short duration of effect.

The following examples were performed to determine which active pharmaceutical ingredient (API), alone or in combination with Brimonidine, will cause an approximate 1-2 mm decrease in the pupillary diameter with an approximate 4 h duration of action (here using a rabbit animal model).

Using the model described in more detail below, the inventors discovered that (1) Phentolamine (comparator API) caused an approximately 1 mm decrease in the pupil at 0.5% and 1% with a duration of at least 6 h; (2) Carbachol was very potent, even at the lowest dose. The duration of action was within a desirable relatively short time frame of 2-4 h; (3) Brimonidine had little to no effect at doses tested; (4) Rivastigmine 1% and Galantamine provided very low effects as compared to carbachol, and addition of Brimonidine did not improve its efficacy; and Galantamine 2% provided similar desirable results as carbachol, but addition of Brimonidine did not improve its efficacy.

Study design: 3 Dutch Belted Rabbits (pigmented breed)/group received a single ocular administration of test articles (one drop per eye) at 3 concentrations (tested one week apart). After a 2-week rest period, combinations were tested. Ocular Irritation was assessed using a modified Draize test. Intraocular pressure (IOP) was measured at baseline, 1 h, 4 h, 6 h and 24 h. Pupillary Diameter was measured at baseline, 15 min, 1 h, 4 h and 6 h after dosing.

Due to the variation in pupillary diameter and IOP between rabbits and between eyes within rabbits, the data for pupillary diameter and IOP were normalized and presented with error bars (SD). A change of 15% to 20% approximates a pupillary diameter change of 1 mm. In human, a reduction of pupillary diameter of about 2 mm is clinically generally desired.

Results: The results were grouped into data for three different concentrations of the API and the tables below provide exemplary treatment scheme for the compounds tested:

Phase 1: Low Dose

| Group ID | No. of Animals | OU Treatment | Treatment Timepoint | Volume/ Route/ Dose Amount | Endpoints |
|---|---|---|---|---|---|
| 1 | 3 | Brimonidine | Day 0 | Topical 1 drop/ eye Low | Ocular Examinations: Baseline (Day −1), 1, 4, 24 and 72 hours post-dose. IOPs: Baseline, 1, 4, 6, 24 and 72 hours post-dose Pupillometry: Baseline, 15, 60, 240, and 360 minutes post-dose |
| 2 | 3 | Rivastigmine | | | |
| 3 | 3 | Galantamine | | | |
| 4 | 3 | Carbachol | | | |
| 5 | 3 | Phentolamine | | | |

Phase 2: Mid-level Dose

| Group ID | No. of Animals | OU Treatment | Treatment Timepoint | Volume/ Route/ Dose Amount | Endpoints |
|---|---|---|---|---|---|
| 6 | 3 | Brimonidine | Day 7 | Topical 1 drop/eye Middle | Ocular Examinations: Baseline (Day −1), 1, 4, 24 and 72 hours post-dose. IOPs: Baseline, 1, 4, 6, 24 and 72 hours post-dose Pupillometry: Baseline, 15, 60, 240, and 360 minutes post-dose |
| 7 | 3 | Rivastigmine | | | |
| 8 | 3 | Galantamine | | | |
| 9 | 3 | Carbachol | | | |
| 10 | 3 | Phentolamine | | | |

Phase 3:

| Group ID | No. of Animals | OU Treatment | Treatment Timepoint | Volume/ Route/ Dose Amount | Endpoints |
|---|---|---|---|---|---|
| 11 | 3 | Brimonidine | Day 14 | Topical 1 drop/eye High | Ocular Examinations: Baseline (Day −1), 1, 4, 24 and 72 hours post-dose. IOPs: Baseline, 1, 4, 6, 24 and 72 hours post-dose Pupillometry: Baseline, 15, 60, 240, and 360 minutes post-dose |
| 12 | 3 | Rivastigmine | | | |
| 13 | 3 | Galantamine | | | |
| 14 | 3 | Carbachol | | | |
| 15 | 3 | Phentolamine | | | |

The treatment schedule for various combination treatments with escalating doses of Rivastigmine are shown in the table below.

| Phase | Treatment | Endpoints |
|---|---|---|
| 5 | Brimonidine tartrate 0.1% + Rivastigmine (0.01%) Brimonidine tartrate 0.1% + Galantamine Hydrobromide (0.02%) | Ocular Examination: Baseline (Day −1), 1, 4, 24 and 72 h post-dose IOP: Baseline (Day −1), 1, 4, 24 and 72 h post-dose Pupillometry: Baseline (Day −1), 1, 4, 24 and 72 h post-dose |
| 6 | Brimonidine tartrate 0.1% + Rivastigmine (0.1%) Brimonidine tartrate 0.1% + Galantamine Hydrobromide (0.2%) | |
| 7 | Brimonidine tartrate 0.1% + Rivastigmine (1%) Brimonidine tartrate 0.1% + Galantamine Hydrobromide (2%) | |

Figure 2:
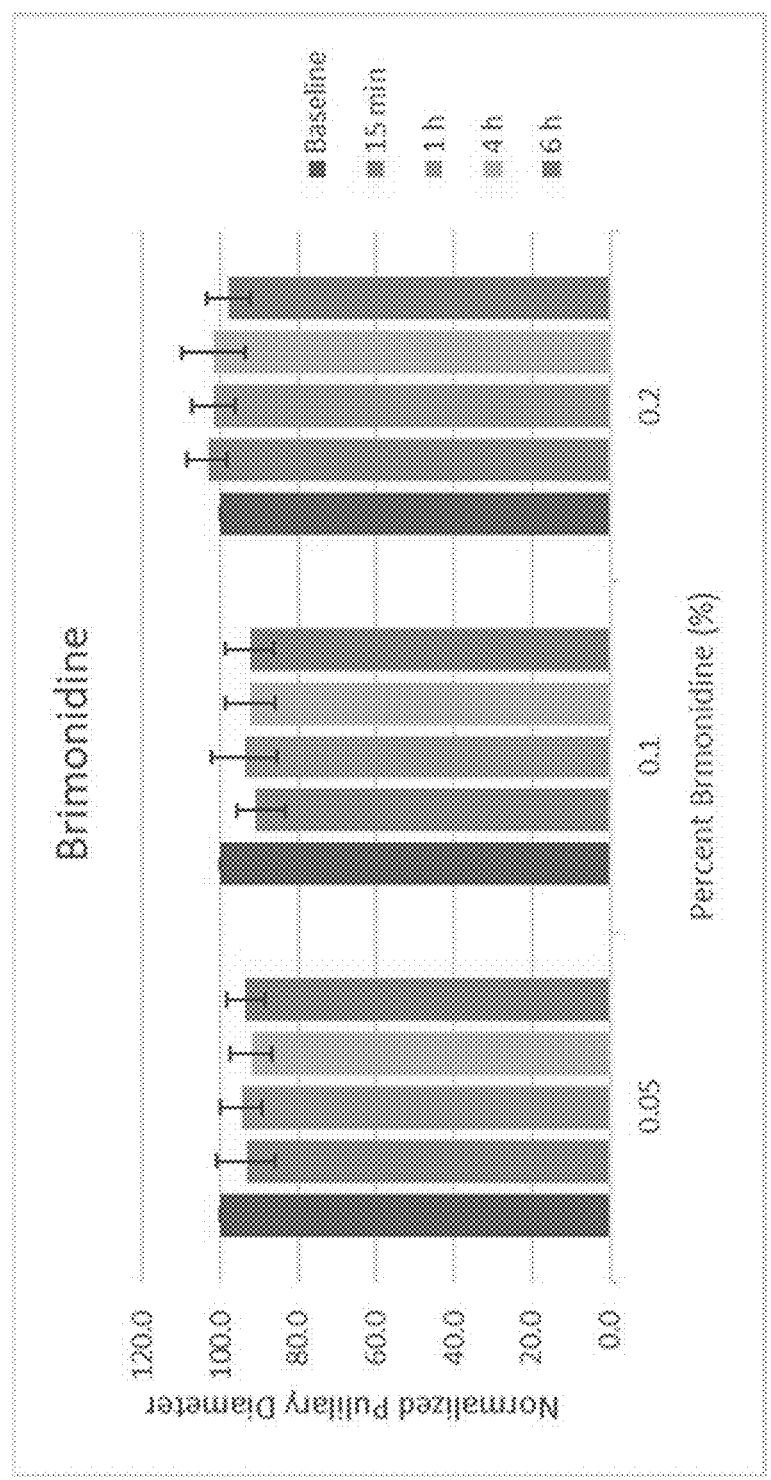
FIG. 2 is a graph depicting strength and duration of miotic effect of brimonidine in a rabbit eye model.
Figure 3A:
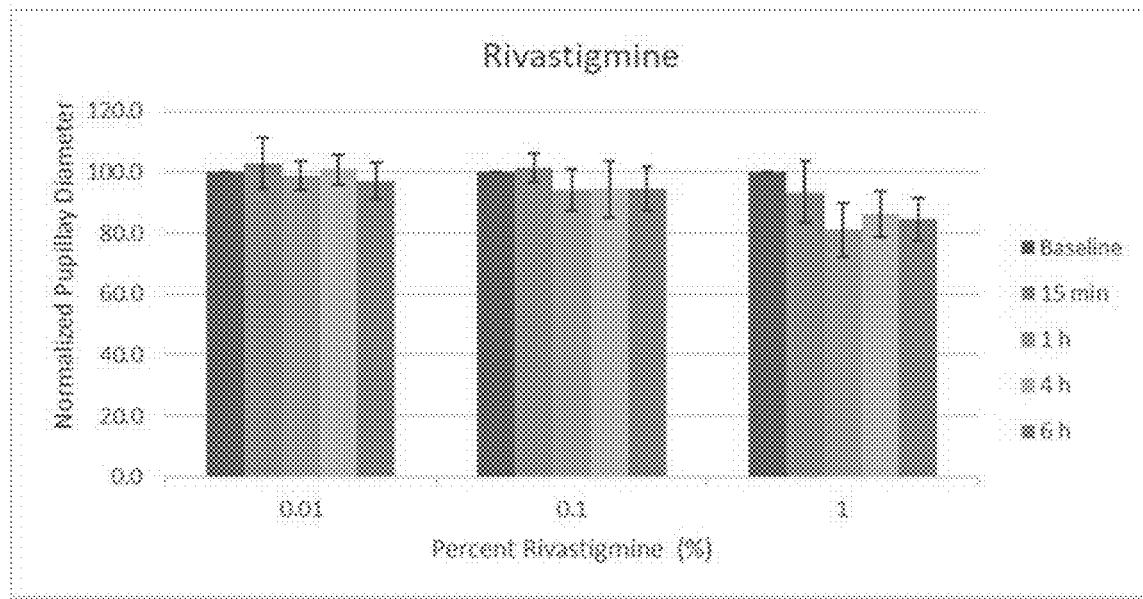
FIGS. 3A and 3B are graphs depicting strength and duration of miotic effect of rivastigmine alone (3A) or rivastigmine in combination with brimonidine (3B) in a rabbit eye model.
Figure 3B:
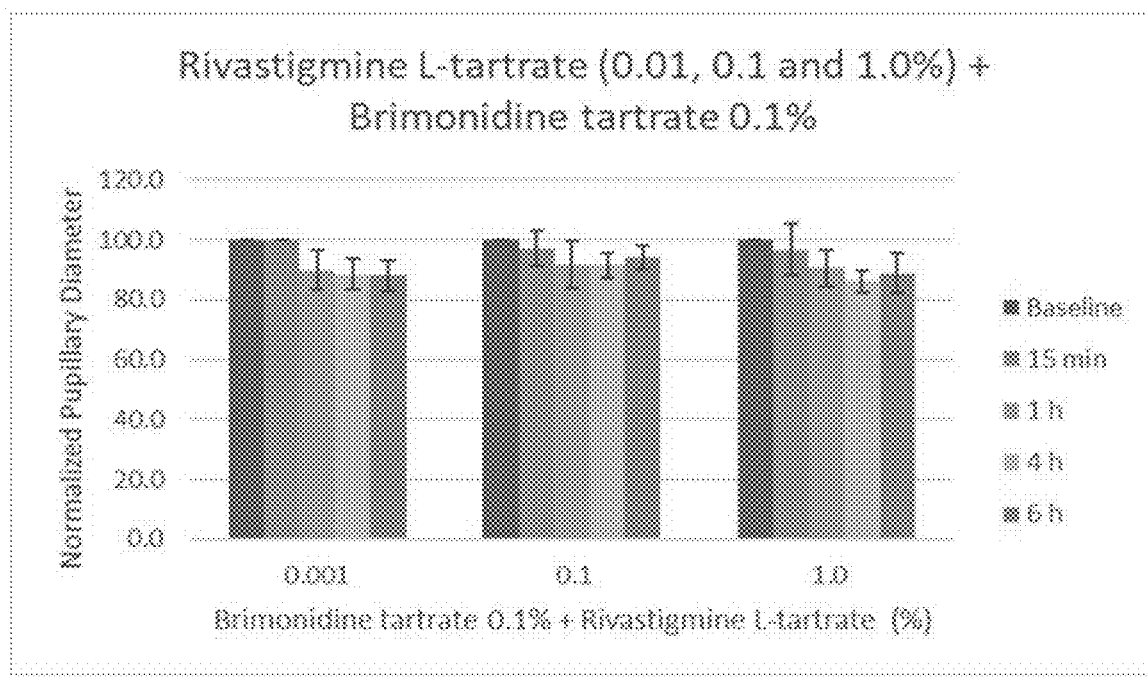
Figure 4A:
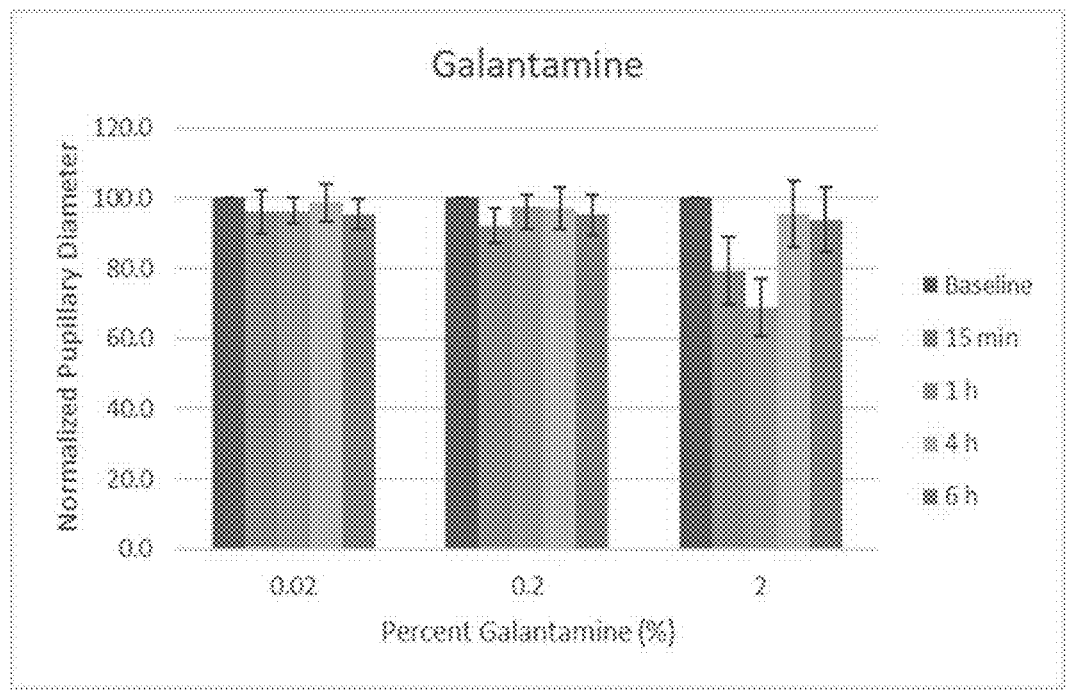
FIGS. 4A and 4B are graphs depicting strength and duration of miotic effect of galantamine alone (4A) or galantamine in combination with brimonidine (4B) in a rabbit eye model.
Figure 4B:
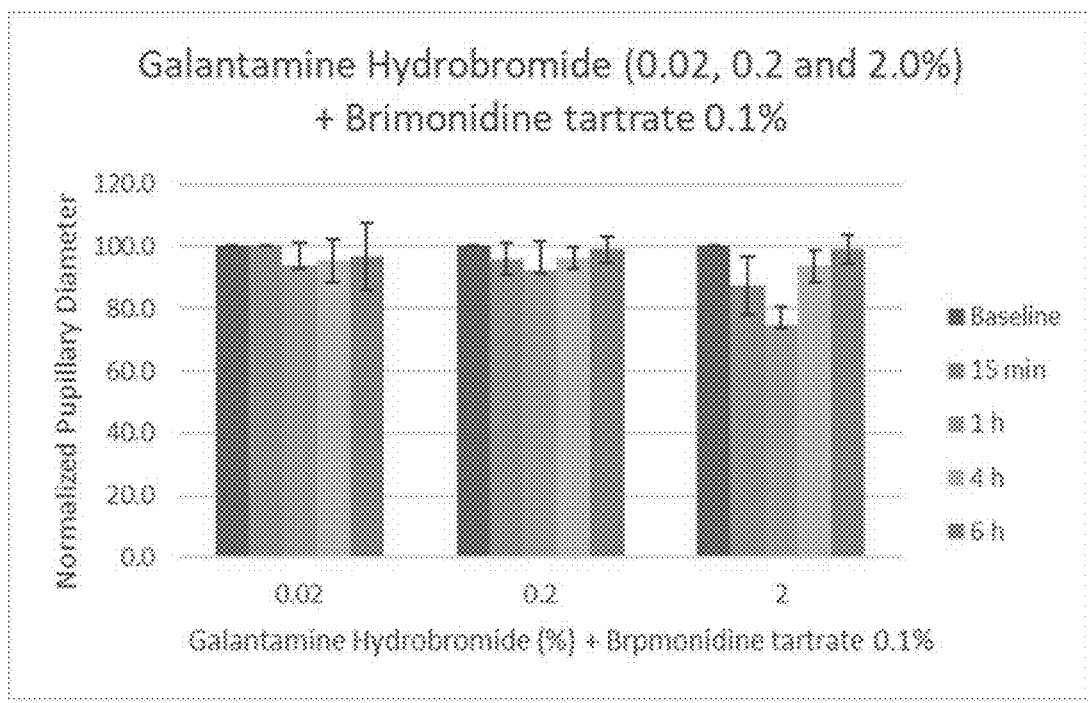
Figure 5:
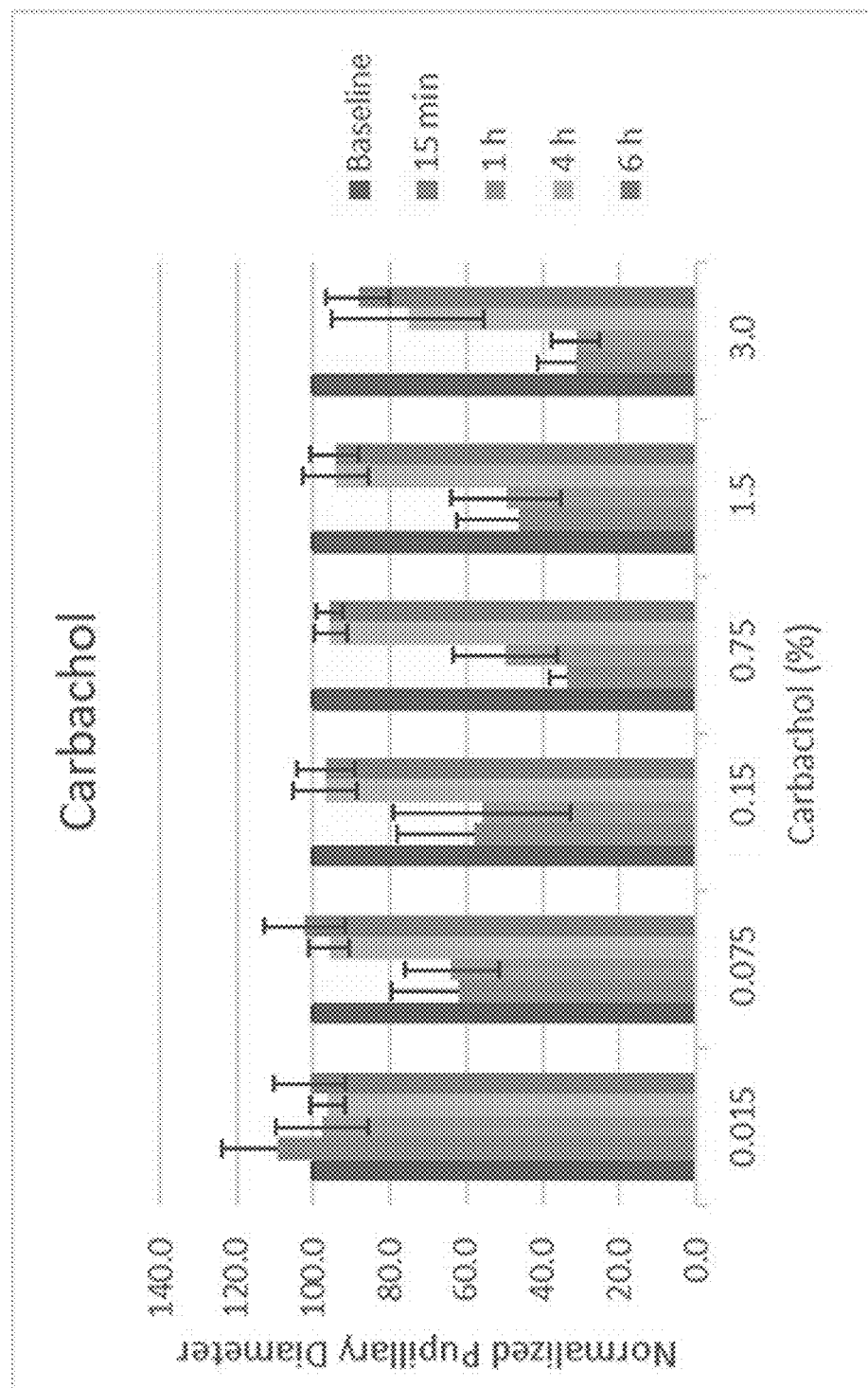
FIG. 5 is a graph depicting strength and duration of miotic effect of carbacachol in a rabbit eye model.

FIG. 1 shows the effect of ocular treatment of phentolamine on pupillary diameter in rabbits. As can be readily seen from the graphs, a reduction in pupillary diameter occurred at all doses and lasted for at least 6 h. FIG. 2 shows the effect of ocular treatment of brimonidine on pupillary diameter in rabbits. Here it is evident that brimonidine had little to no effect at low doses tested. FIG. 3 depicts the effect of ocular treatment of rivastigmine alone and in combination with brimonidine on pupillary diameter in rabbits. As is readily evident, Rivastigmine 1% alone performed substantially similar to Phentolamine (comparator), and the addition of Brimonidine had no effect. FIG. 4 shows the effect of ocular treatment of galantamine alone and in combination with brimonidine on pupillary diameter in rabbits. As can be taken from the graphs, a reduction in pupillary diameter occurred at the high dose (2%) and lasted for at least 1-3 h, and Brimonidine did not add to the effect. FIG. 5 depicts the effect of carbachol on pupillary diameter in rabbits. As can be readily appreciated from the graph in FIG. 5, Carbachol was very potent, even at a low concentration of about 0.075% in the rabbit. Advantageously, the duration of action was relatively short, at between about 1-3 h.

Phentolamine, the comparator, caused an approximately 1 mm decrease in the pupil at 0.5% and 1% with a duration of at least 6 h, and Carbachol was very potent, even at low doses of about 0.075% Notably, Brimonidine had little to no effect at doses tested, while Rivastigmine at 1% alone had desirable effect (1 mm decrease lasting at least 6 h) and Galantamine 2% alone had desirable effect (1-2 mm decrease lasting at least 1 h). Brimonidine did not improve the efficacy of Rivastigmine or Galantamine. Beneficially, treatment with the tested compounds did not affect the TOP (minimal changes) nor cause ocular irritation.

Figure 6A:
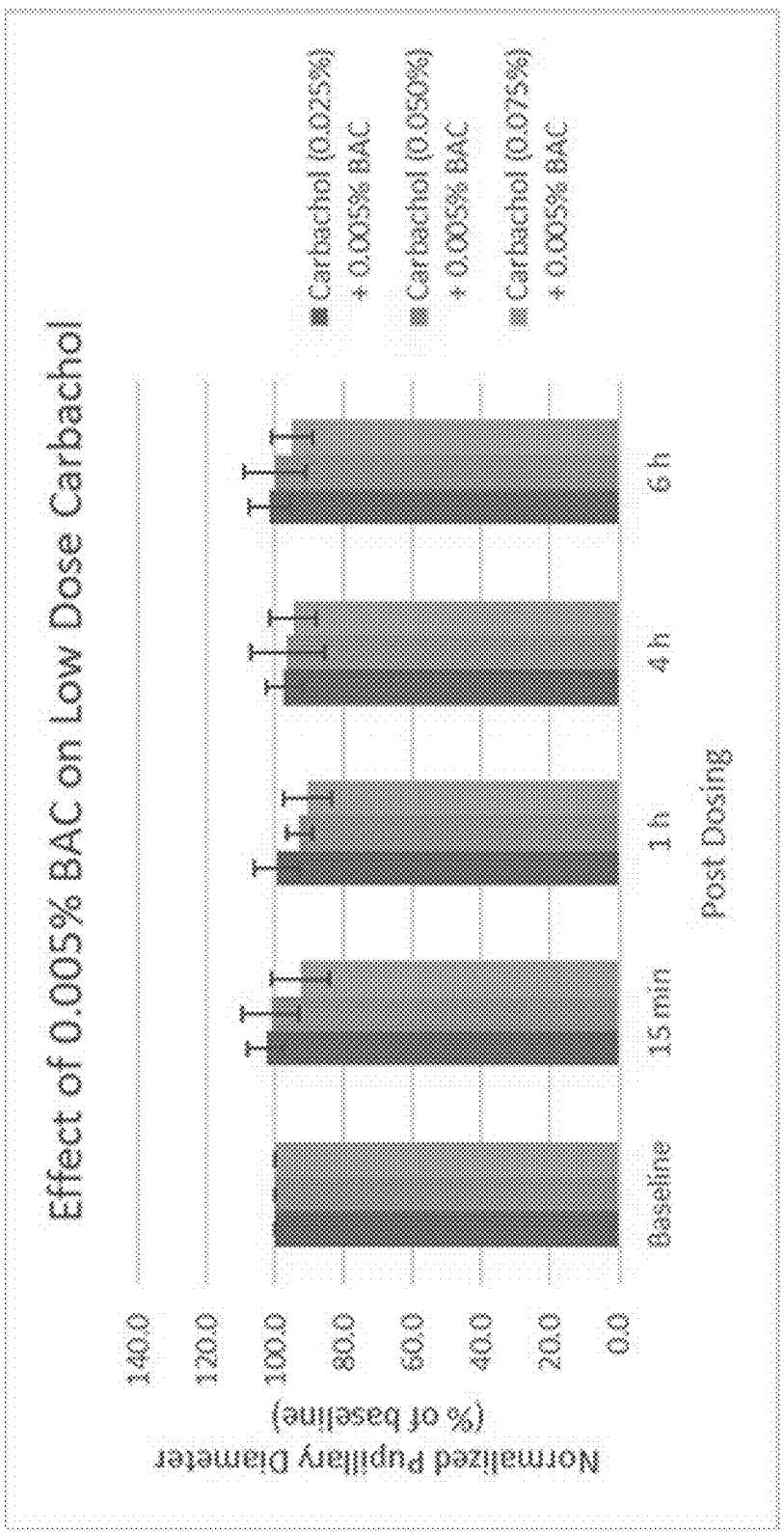
FIGS. 6A-6C are graphs depicting the effect of benzalkonium chloride on carbachol effect at varying concentrations of benzalkonium chloride.
Figure 6B:
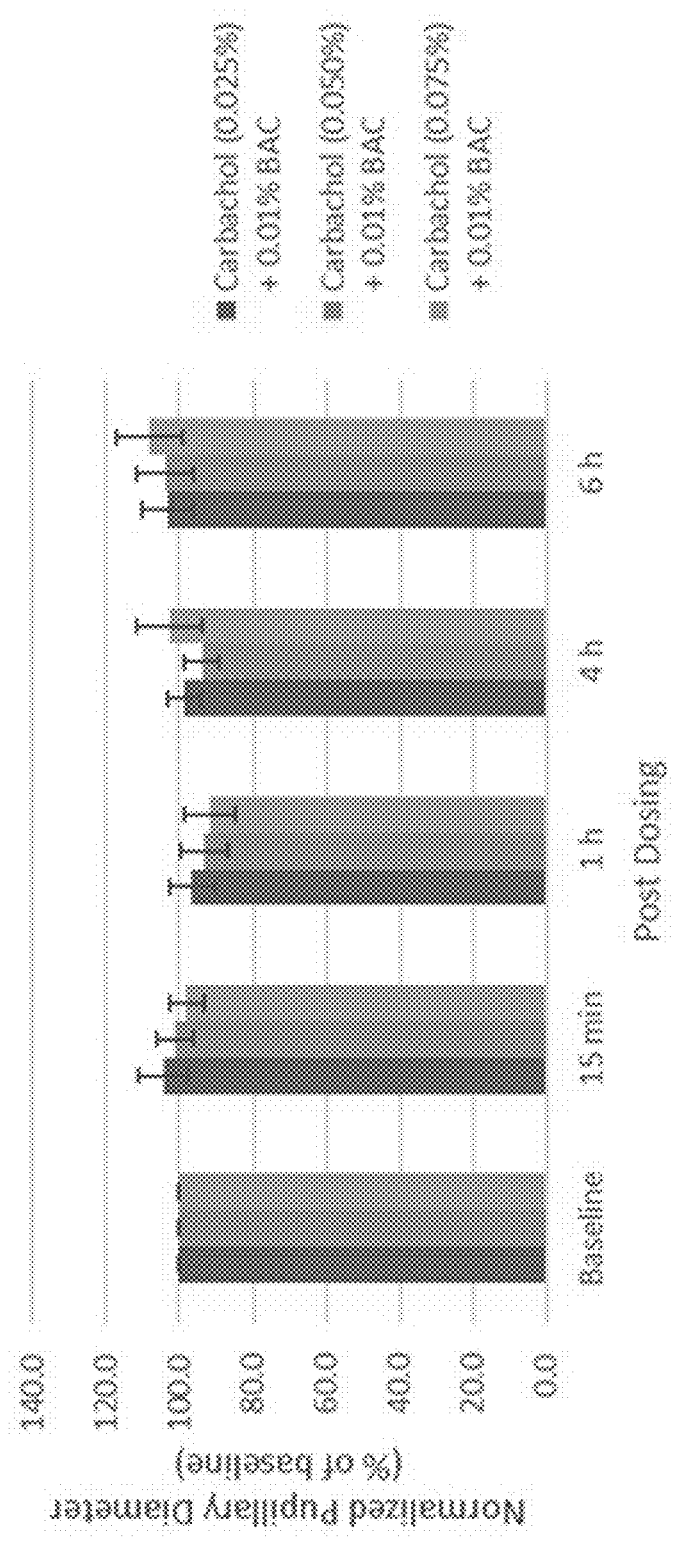
Figure 6C:
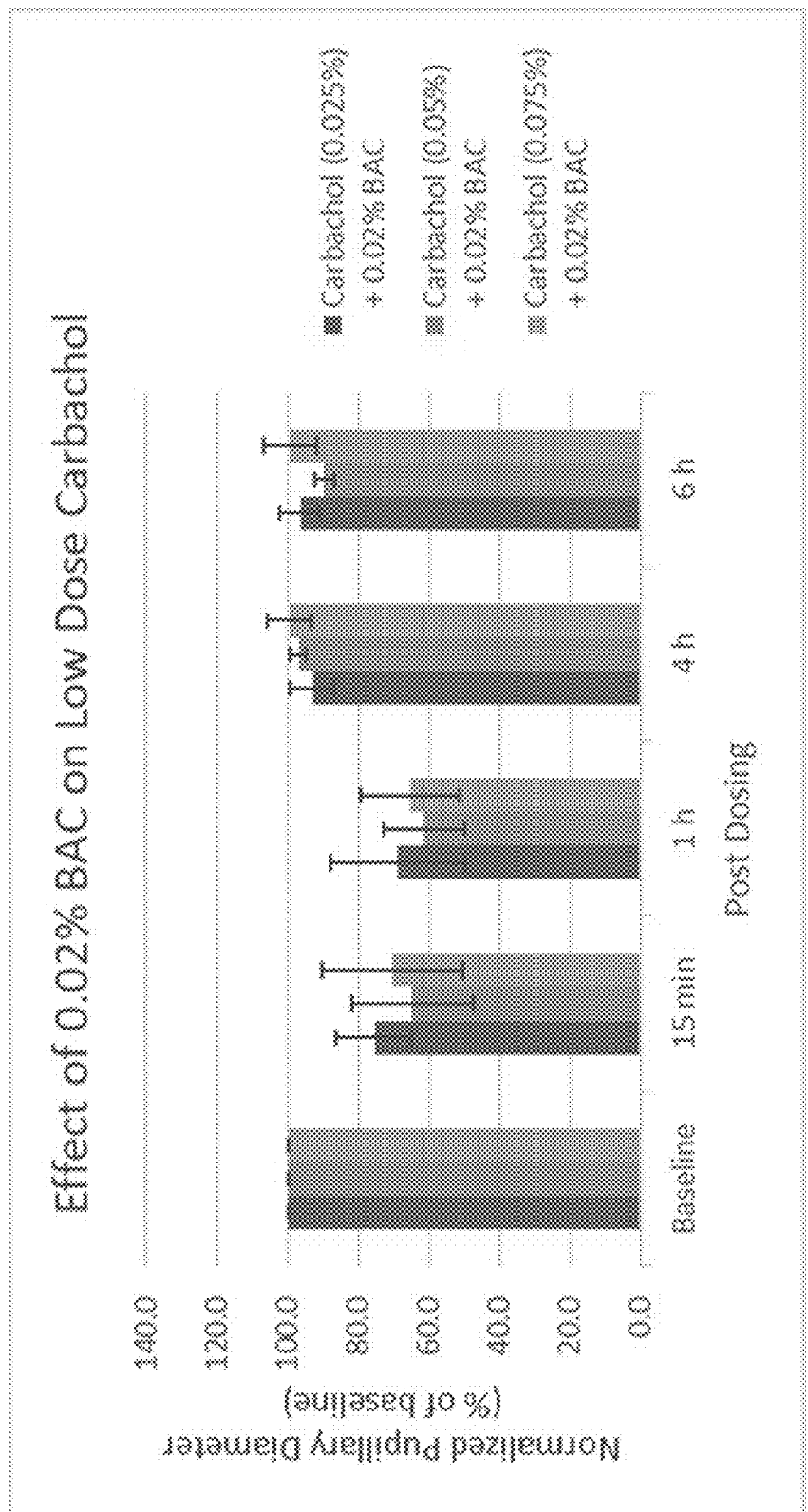

In still further experiments, the inventors investigated the effect of benzalkonium chloride on the miotic effect of carbachol. To that end, different concentrations of BAC were employed between 0.005% and 0.02% at carbachol concentrations between 0.025% and 0.075%, and the results are shown in FIGS. 6A-6C. More specifically, FIG. 6A shows the results for BAC at 0.005%, FIG. 6B results for BAC at 0.01%, and FIG. 6C shows the results for BAC at 0.005%. As can be readily seen from the graphs, BAC at a concentration of 0.005% had minimal effect with some effect seen at 1 hr at the higher carbachol concentration. The effect of BAC was somewhat more pronounced at a concentration of 0.01%, and the effect of BAC at a concentration of at least 0.02% was significant as is evident from the data in FIG. 6C.

To optimize the concentration of carbachol in the topical ophthalmic formulations, the inventors tested various dosages, and the table below depicts the composition for the carbachol formulations used. The table below shows the general composition of the formulations used in the examples below, with specific concentrations of selected ingredients noted in the respective examples.

| Ingredient | Grade | Function | Quantity % (mg/mL) |
|---|---|---|---|
| Carbachol | USP | API | 0.02-3.0% (0.2-30 mg/mL) |
| Sodium Chloride | USP | Tonicity agent | 0.05-0.9% (0.5-9.0 mg/mL) |
| Hypromellose 2910 | USP | Viscosity modifier | 0.2-1.0% (2-10 mg/mL) |
| Boric Acid | USP | Buffering agent | (0.02-0.62%) 0.2-6.2 mg/mL |
| Sodium Hydroxide | USP | pH adjuster | q.s. to pH 5.5-7.5 |
| Benzalkonium Chloride | USP | Preservative | 0.05-0.02% (0.5-0.2 mg/mL) |
| Water for Injection | NF | Vehicle | q.s. to 100% (1.0 mL) |

Figure 7:
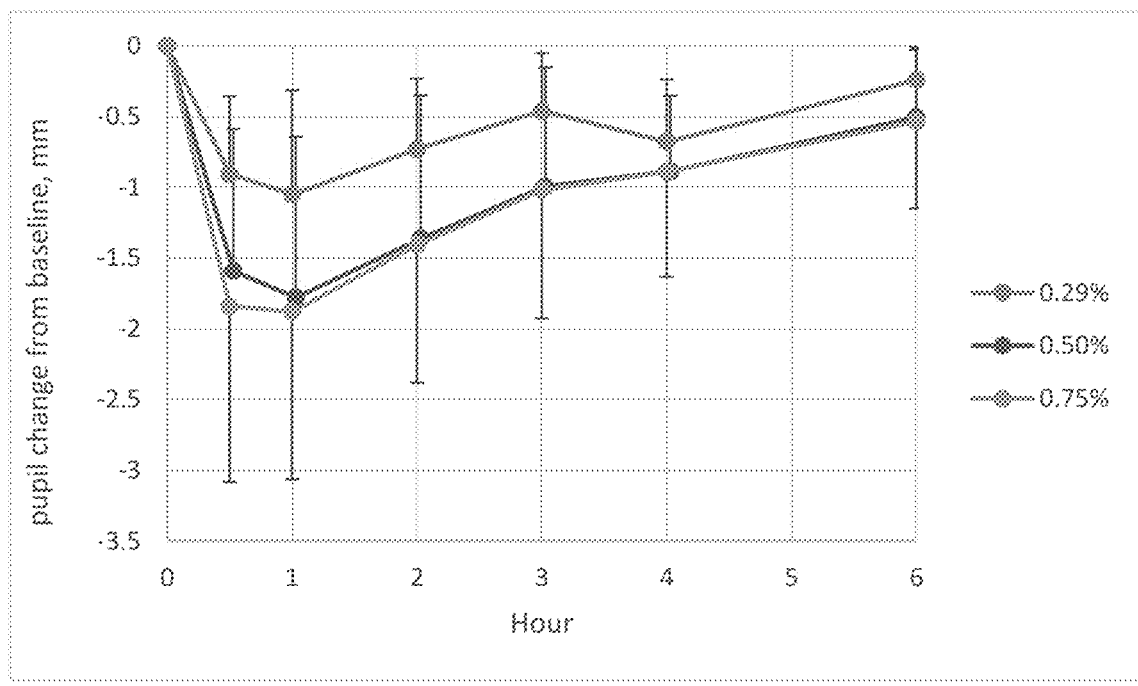
FIG. 7 is a graph depicting exemplary results for a dose response in human using a carbachol formulation according to the inventive subject matter.
Figure 8:
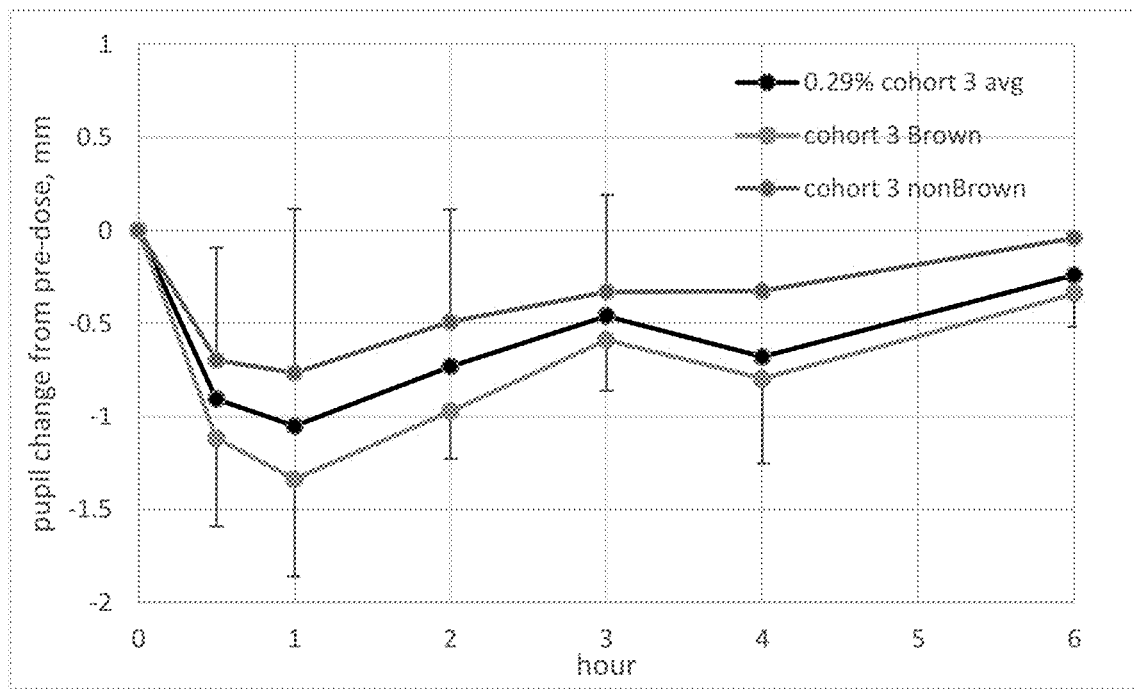
FIG. 8 is a graph depicting exemplary results for miotic response in human individuals of different eye color using a 0.29% carbachol formulation according to the inventive subject matter.
Figure 9:
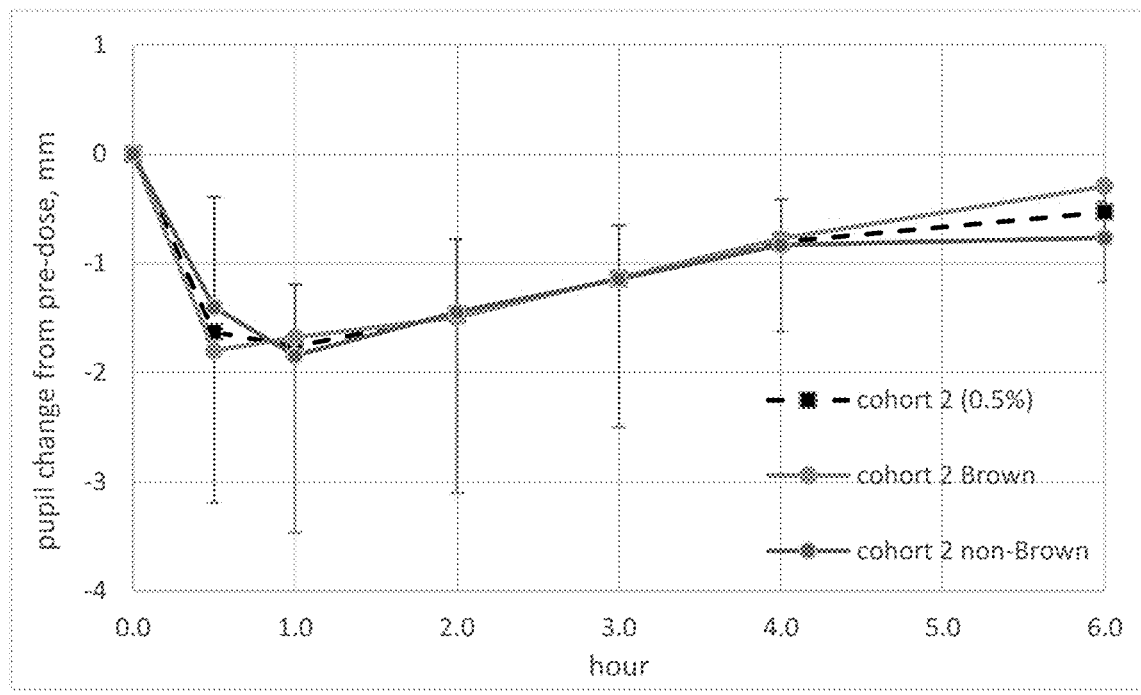
FIG. 9 is a graph depicting exemplary results for miotic response in human individuals of different eye color using a 0.50% carbachol formulation according to the inventive subject matter.
Figure 10:
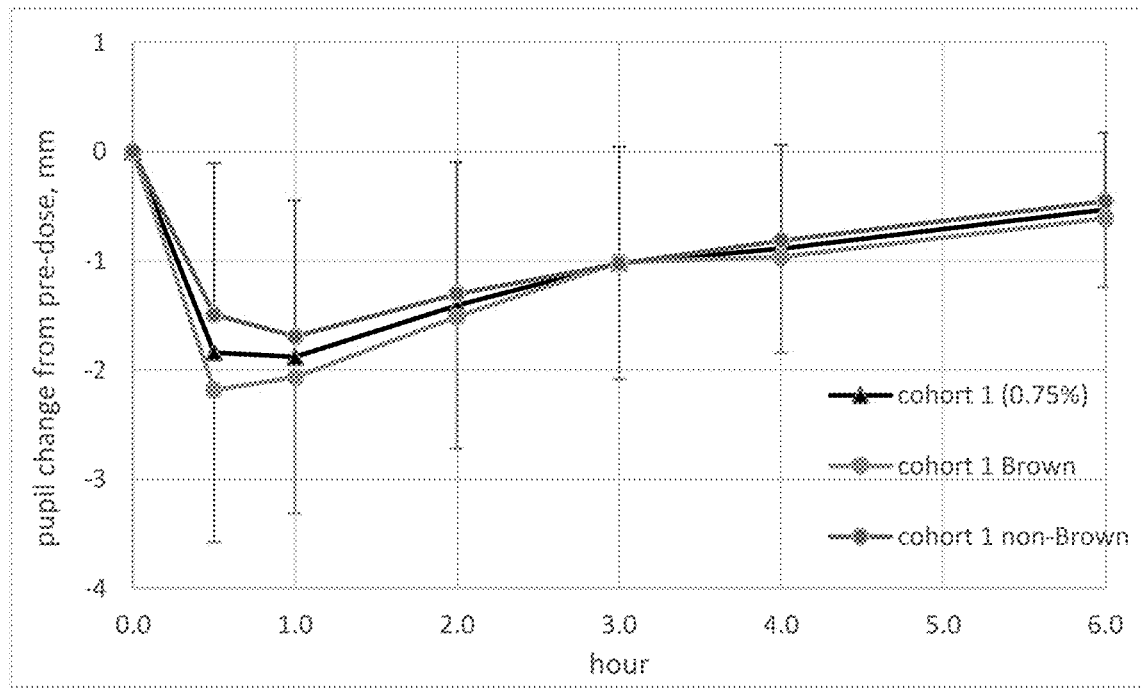
FIG. 10 is a graph depicting exemplary results for miotic response in human individuals of different eye color using a 0.75% carbachol formulation according to the inventive subject matter.

Exemplary results for the miotic effect of carbachol at 0.29%, 0.50%, and 0.75% are depicted in FIG. 7. As can be readily seen, an acute and transient miotic effect was achieved with all concentrations. Notably, the average change in pupil size at 0.5% showed efficacy through Hour 3 from a single dose and a further increase in concentration to 0.75% did not increase the miotic effect. In contrast, concentrations lower than 0.5% had reduced miotic effect. Therefore, carbachol in the tested formulations had a saturation of dose response at 0.5%. Miotic response was also assessed at the three different concentrations in regard to eye color and FIG. 8 shows exemplary results for a carbachol concentration of 0.29%, FIG. 9 shows exemplary results for a carbachol concentration of 0.50%, and FIG. 10 shows exemplary results for a carbachol concentration of 0.75%. As can be taken from the graphs, miotic effect was independent of the eye color at all three tested concentrations.

The inventors further investigated the influence of buffer strength and packaging materials for contemplated compositions on stability for pH and viscosity. More particularly, the inventors tested various buffer strengths and polymeric materials and glass containers. The results in Tables below show data for pH 6.5 and pH 7.0 at buffer concentrations between 10 and 100 mM for Inden Pharma polymeric bottles.

| Concentration of Boric acid(mM) | Required pH of formulation | Adjusted pH | T = 0 | 2 week - 40° C./ 75% RH | 1 Month - 40° C./ 75% RH |
|---|---|---|---|---|---|
| 10 | 6.5 | 6.5 | 6.04 | 5.88 | 5.91 |
| 25 | 6.5 | 6.53 | 6.36 | 6.26 | 6.35 |
| 50 | 6.5 | 6.52 | 6.4 | 6.31 | 6.39 |
| 100 | 6.5 | 6.5 | 6.43 | 6.29 | 6.38 |

| Concentration of Boric acid(mM) | Required pH of formulation | Adjusted pH | T = 0 | 2 week - 40° C./ 75% RH | 1 Month - 40° C./ 75% RH |
|---|---|---|---|---|---|
| 10 | 7 | 6.99 | 6.7 | 6.56 | 6.71 |
| 25 | 7 | 6.99 | 6.84 | 6.73 | 6.84 |
| 50 | 7 | 7 | 6.89 | 6.79 | 6.9 |
| 100 | 7 | 7 | 6.94 | 6.81 | 6.91 |

| Concentration of Boric acid (mM) | Required pH of formulation | Viscosity T = 0 | Viscosity 2 week - 40° C./ 75% RH | Viscosity 1 Month - 40° C./ 75% RH |
|---|---|---|---|---|
| 10 | 6.5 | 204.97 | 216.13 | 232.2 |
| 25 | 6.5 | 210.83 | 219.5 | 237.2 |
| 50 | 6.5 | 200.93 | 204.93 | 213.9 |
| 100 | 6.5 | 200.15 | 195.3 | 205.6 |

| Concentration of Boric acid (mM) | Required pH of formulation | Viscosity T = 0 | Viscosity 2 week - 40° C./ 75% RH | Viscosity 1 Month - 40° C./ 75% RH |
|---|---|---|---|---|
| 10 | 7 | 185.6 | 186.67 | 192.5 |
| 25 | 7 | 201.23 | 218.6 | 242.8 |
| 50 | 7 | 206.35 | 219.2 | 227 |
| 100 | 7 | 207.45 | 236.3 | 225.4 |

The results in Tables below show data for pH 6.5 and pH 7.0 at buffer concentrations between 10 and 100 mM for Medidose bottles.

| Concentration of Boric acid(mM) | Required pH of formulation | Adjusted pH | T = 0 | 2 week - 40° C./ 75% RH | 1 Month - 40° C./ 75% RH |
|---|---|---|---|---|---|
| 10 | 6.5 | 6.5 | 6.04 | 5.67 | 5.29 |
| 25 | 6.5 | 6.53 | 6.36 | 6.1 | 5.8 |
| 50 | 6.5 | 6.52 | 6.4 | 6.28 | 6.22 |
| 100 | 6.5 | 6.5 | 6.43 | 6.33 | 6.25 |

| Concentration of Boric acid(mM) | Required pH of formulation | Adjusted pH | T = 0 | 2 week - 40° C./ 75% RH | 1 Month - 40° C./ 75% RH |
|---|---|---|---|---|---|
| 10 | 7 | 6.99 | 6.7 | 6.43 | 6.27 |
| 25 | 7 | 6.99 | 6.84 | 6.67 | 6.61 |
| 50 | 7 | 7 | 6.89 | 6.84 | 6.76 |
| 100 | 7 | 7 | 6.94 | 6.82 | 6.81 |

| Concentration of Boric acid(mM) | Required pH of formulation | T = 0 | Viscosity 2 week - 40° C./ 75% RH | Viscosity 1 Month - 40° C./ 75% RH |
|---|---|---|---|---|
| 10 | 6.5 | 204.97 | 188.5 | 181.4 |
| 25 | 6.5 | 210.83 | 189.13 | 181.1 |
| 50 | 6.5 | 200.93 | 185.7 | 175.8 |
| 100 | 6.5 | 200.15 | 170.23 | 158.77 |

| Concentration of Boric acid(mM) | Required pH of formulation | T = 0 | Viscosity 2 week - 40° C./ 75% RH | Viscosity 1 Month - 40° C./ 75% RH |
|---|---|---|---|---|
| 10 | 7 | 185.6 | 162.5 | 161.57 |
| 25 | 7 | 201.23 | 181.4 | 173 |
| 50 | 7 | 206.35 | 187.3 | 175.8 |
| 100 | 7 | 207.45 | 185.4 | 172.1 |

The results in Tables below show data for pH 6.5 and pH 7.0 at buffer concentrations between 10 and 100 mM for glass containers.

| Concentration of Boric acid(mM) | Required pH of formulation | Adjusted pH | T = 0 | 2 week - 40° C./ 75% RH | 1 Month - 40° C./ 75% RH |
| --- | --- | --- | --- | --- | --- |
| 10 | 6.5 | 6.5 | 6.04 | 6.26 | 6.43 |
| 25 | 6.5 | 6.53 | 6.36 | 6.5 | 6.53 |
| 50 | 6.5 | 6.52 | 6.4 | 6.49 | 6.48 |
| 100 | 6.5 | 6.5 | 6.43 | 6.44 | 6.44 |

| Concentration of Boric acid(mM) | Required pH of formulation | Adjusted pH | T = 0 | 2 week - 40° C./ 75% RH | 1 Month - 40° C./ 75% RH |
| --- | --- | --- | --- | --- | --- |
| 10 | 7 | 6.99 | 6.7 | 6.75 | 7.04 |
| 25 | 7 | 6.99 | 6.84 | 6.92 | 6.93 |
| 50 | 7 | 7 | 6.89 | 6.93 | 6.92 |
| 100 | 7 | 7 | 6.94 | 6.91 | 6.9 |

| Concentration of Boric acid(mM) | Required pH of formulation | T = 0 | Viscosity 2 week - 40° C./ 75% RH | Viscosity 1 Month - 40° C./ 75% RH |
| --- | --- | --- | --- | --- |
| 10 | 6.5 | 204.97 | 187.9 | 181.4 |
| 25 | 6.5 | 210.83 | 190.7 | 181.4 |
| 50 | 6.5 | 200.93 | 179.5 | 172.1 |
| 100 | 6.5 | 200.15 | 169.3 | 160 |

| Concentration of Boric acid(mM) | Required pH of formulation | T = 0 | Viscosity 2 week - 40° C./ 75% RH | Viscosity 1 Month - 40° C./ 75% RH |
| --- | --- | --- | --- | --- |
| 10 | 7 | 185.6 | 161.57 | 157.2 |
| 25 | 7 | 201.23 | 183.2 | 174.9 |
| 50 | 7 | 206.35 | 181.4 | 172.1 |
| 100 | 7 | 207.45 | 189.13 | 181.7 |

As can be seen from the above results, pH drift and change in viscosity was observed, and formulations with higher buffer concentrations (at or above 50 mM) had less deviation of pH and viscosity than those with lower buffer concentrations (below 50 mM). Notably, where an ethylene oxide sterilized polypropylene container was used, a pH drift was observed from an initial pH of 6.5-7.0 to a pH of between 3.7 and 3.9 after 3 months of storage at 25° C./40% RH and 40° C./25% RH, respectively.

Unless otherwise noted throughout the disclosure, all percentages are weight percent (w/w). In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. Most typically, where a numeral is qualified by the term "about", a range of the numeric value +/−10% (inclusive) of the numeral is contemplated. Moreover, the recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of acute and transient treatment of night vision disturbance in an individual, comprising:
   topically administering a carbachol composition to an eye of an individual to reduce pupillary diameter by about 2 mm;
      wherein the carbachol is present in the composition in an amount of equal or less than about 0.75%;

wherein the carbachol composition further comprises benzalkonium chloride in an amount of about 0.02%; and wherein the carbachol composition has a pH of between about 6.5 and about 7.0 and a viscosity of between about 170 cP to about 220 cP.

2. The method of claim 1, wherein the carbachol is present in the composition in an amount of equal or less than about 0.50%.

3. The method of claim 1, wherein the carbachol is present in the composition in an amount of between about 0.25% and about 0.50%.

4. The method of claim 1, wherein the carbachol composition has a pH of about 7.0 and a viscosity of between about 180 cP to about 190 cP.

5. The method of claim 1, wherein a miotic effect of the composition is equal or less than 30% reduction in pupillary diameter.

6. The method of claim 1, wherein the treatment reduces at least one of glare, starburst, halo, and double vision.

7. The method of claim 1, wherein the composition further comprises a borate buffer and/or sodium chloride as tonicity agent.

8. The method of claim 1, wherein the individual has not undergone refractive surgery.

9. The method of claim 1, wherein the acute and transient treatment has a duration of equal or less than 3 hours at a reduction of pupillary diameter of about 2 mm.

10. The method of claim 1, wherein the acute and transient treatment is an on-demand and non-curative treatment.

* * * * *